United States Patent
Burk et al.

(10) Patent No.: US 9,315,486 B2
(45) Date of Patent: Apr. 19, 2016

(54) THERAPEUTIC CYCLOPENTANOLS, COMPOSITIONS THEREOF, AND METHODS FOR USE THEREOF

(71) Applicant: Allergan, Inc., Irvine, CA (US)

(72) Inventors: Robert M. Burk, Laguna Beach, CA (US); Todd S. Gac, Santa Ana, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 14/527,387

(22) Filed: Oct. 29, 2014

(65) Prior Publication Data

US 2015/0119454 A1   Apr. 30, 2015

Related U.S. Application Data

(60) Provisional application No. 61/896,970, filed on Oct. 29, 2013, provisional application No. 61/896,979, filed on Oct. 29, 2013.

(51) Int. Cl.
*C07D 333/06* (2006.01)
*C07D 333/38* (2006.01)

(52) U.S. Cl.
CPC .................. *C07D 333/38* (2013.01)

(58) Field of Classification Search
CPC ................................................ C07D 333/06
See application file for complete search history.

(56) References Cited

U.S. PATENT DOCUMENTS

| | | | |
|---|---|---|---|
| 4,166,452 | A | 9/1979 | Generales, Jr. |
| 4,256,108 | A | 3/1981 | Theeuwes |
| 4,265,874 | A | 5/1981 | Bonsen et al. |
| 7,427,685 | B2 | 9/2008 | Donde et al. |
| 7,429,669 | B2 | 9/2008 | Old et al. |
| 8,158,676 | B2 | 4/2012 | Burk |
| 8,455,547 | B2 | 6/2013 | Burk |
| 8,546,603 | B2 | 10/2013 | Burk |

OTHER PUBLICATIONS

Remington's Pharmaceutical Sciences, Mack Publishing Company, Easton, Pa., 16th Edition, 1980.
Guillory, J. Keith, Generation of Polymorphs, Hydrates, Solvates, and Amorphous Solids, Polymorphism in Pharmaceutical Solids,1999, 10th Ed., Chapter 5.

*Primary Examiner* — Bruck Kifle
(74) *Attorney, Agent, or Firm* — Jonathan Bass

(57) ABSTRACT

Described herein are well-defined cyclopentanols useful for treating glaucoma and ocular hypertension.

18 Claims, No Drawings

THERAPEUTIC CYCLOPENTANOLS, COMPOSITIONS THEREOF, AND METHODS FOR USE THEREOF

CROSS-REFERENCE TO RELATED APPLICATIONS

This application is a non-provisional application claiming the benefit of U.S. provisional application 61/896,970 filed on Oct. 29, 2013, and U.S. 61/896,979 filed on Oct. 29, 2013, each of which is incorporated by reference in their entirety and serve as the basis for a priority claim of the present application.

FIELD

The present invention relates generally to compounds and methods for treating ocular disorders. The invention relates specifically to the use of certain well-defined cyclopentanols for the treatment of ocular hypertension and glaucoma.

BACKGROUND

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

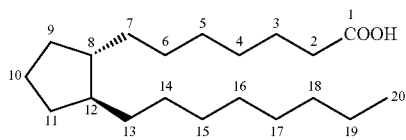

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin E1 (PGE1), prostaglandin E2 (PGE2)], and on the configuration of the substituents on the alicyclic ring indicated by α or β [e.g. prostaglandin F2α (PGF2β)].

SUMMARY

The invention provides well-defined cyclopentanols useful for treating glaucoma and ocular hypertension.

In one aspect of the invention, there are described herein compounds having the structure:

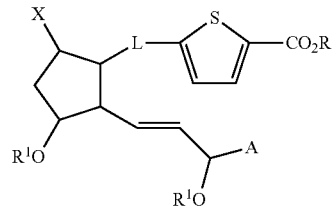

or pharmaceutically acceptable salts, hydrates, solvates, isomers, tautomers, enantiomers, and diastereomers thereof, wherein:

R is H; $C_1$ to $C_{10}$ alkyl; $C_1$ to $C_{10}$ alkyl bearing at least one hydroxyl substituent; —$(CH_2)R^a$, wherein $R^a$ is $C_5$ to $C_{10}$ cycloalkyl; aryl; benzyl; —$CH_2CH_2OR^1$; —$CH(CH_2OR^1)_2$, —$C(CH_2OR^1)_3$, or $CH_2CH_2N(R^1)_2$; or when R is —$CH_2CH_2N(R^1)_2$, each $R^1$ can be taken together to form a heterocyclic ring;

$R^1$ is H, $C_1$ to $C_{10}$ alkyl, —COR, or —$CO_2R$;

X is halogen, CN, OH, SH, =$CHR^1$;

A is $C_1$ to $C_{10}$ alkyl bearing at least one hydroxyl substituent; and

L is $C_1$-$C_6$ alkylene wherein optionally at least one $CH_2$ unit can be replaced with O or S;

with the proviso that the compound:

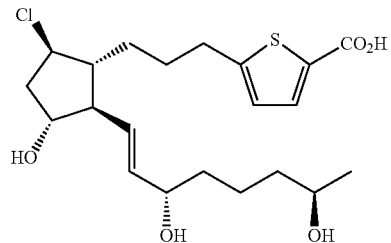 [SMILES: C[C@@H](O)CCC[C@H](O)/C=C/[C@@H]1[C@@H](CCCc2ccc(C(=O)O)s2)[C@H](Cl)C[C@H]1O]

is not included.

In another aspect of the invention, there are described herein compositions including at least one compound of the invention, wherein the composition is a liquid which is ophthalmically acceptable.

In another aspect of the invention there are described herein methods for treating glaucoma or ocular hypertension. Such methods can be performed, for example, by administering to a subject in need thereof a therapeutically effective amount of a compound of the invention.

In still another aspect of the invention, there are described herein kits including at least one composition of the invention, a container, and instructions for administration of the composition to a subject in need thereof for the treatment of glaucoma or ocular hypertension.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques can be used for chemical syntheses, chemical analyses, and formulation.

As used herein, "alkyl" refers to straight or branched chain hydrocarbyl groups having from 1 up to about 100 carbon atoms. Whenever it appears herein, a numerical range, such as "1 to 100" or "$C_1$-$C_{100}$", refers to each integer in the given range; e.g., "$C_1$-$C_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated. For example, the term "alkyl" can refer to a sub-range between $C_1$-$C_{100}$ (e.g. $C_1$-$C_6$). "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, lower alkylamino, lower alkyldiamino, amido, azido, —C(O)H, —C(O)R$_7$, —CH$_2$OR$_7$, —OC(O)O wherein R$_7$ is H or lower alkyl, acyl, oxyacyl, carboxyl, carbamate, sulfonyl, sulfonamide, sulfuryl, and the like. As used herein, "lower alkyl" refers to alkyl moieties having from 1 to about 6 carbon atoms.

As used herein, "alkylene" refers to a divalent alkyl moiety that connects to two distinct portions of the molecule. Exemplary alkylenes include, for example, —CH$_2$— (methylene), —(CH$_2$)$_2$— (ethylene), —(CH$_2$)$_3$— (propylene), —(CH$_2$)$_4$— (butylene), and others that would be apparent to a skilled person.

As used herein, "alkenyl" refers to straight or branched chain hydrocarbyl groups having at least one carbon-carbon double bond, and having in the range of about 2 up to about 100 carbon atoms, and "substituted alkenyl" refers to alkenyl groups further bearing one or more substituents as set forth above. As used herein, "lower alkenyl" refers to alkenyl moieties having from 2 to about 6 carbon atoms.

As used herein, "alkynyl" refers to straight or branched chain hydrocarbyl groups having at least one carbon-carbon triple bond, and having in the range of about 2 up to about 100 carbon atoms, and "substituted alkynyl" refers to alkynyl groups further bearing one or more substituents as set forth above. As used herein, "lower alkynyl" refers to alkynyl moieties having from 2 to about 6 carbon atoms.

As used herein, "cycloalkyl" refers to cyclic (i.e., ring-containing) alkyl moieties typically containing in the range of about 3 up to about 10 carbon atoms, and "substituted cycloalkyl" refers to cycloalkyl groups further bearing one or more substituents as set forth above.

As used herein, "aryl" refers to aromatic groups having in the range of 5 up to 14 carbon atoms and "substituted aryl" refers to aryl groups further bearing one or more substituents as set forth above.

As used herein, "heteroaryl" refers to aromatic moieties containing one or more heteroatoms (e.g., N, O, S, or the like) as part of the ring structure and having in the range of 5 up to 14 total atoms in the ring structure (i.e., carbon atoms and heteroatoms). "Substituted heterocyclic" refers to heterocyclic groups further bearing one or more substituents as set forth above.

As used herein, "heterocyclic" refers to non-aromatic cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As used herein, "halogen" or "halide" refers to fluoride, chloride, bromide or iodide. "Fluoride", "chloride", "bromide", or "iodide" can also be referred to as "fluoro", "chloro", "bromo", or "iodo", respectively.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures as well as scalemic mixtures. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Some of the compounds of the invention may form salts with pharmaceutically acceptable acids or bases, and such pharmaceutically acceptable salts of the compounds described herein are also within the scope of the invention.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Exemplary ions include, for example, the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring. Salts can form from or incorporate one or more deprotonated acidic groups (e.g. carboxylic acids), one or more protonated basic groups (e.g. amines), or both (e.g. zwitterions).

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted.

In one aspect of the invention, there are described herein compounds having the structure:

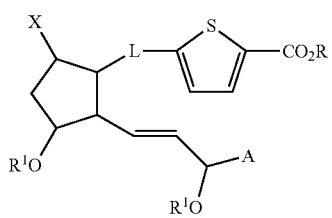

or pharmaceutically acceptable salts, hydrates, solvates, isomers, tautomers, enantiomers, and diastereomers thereof, wherein:

R is H; $C_1$ to $C_{10}$ alkyl; $C_1$ to $C_{10}$ alkyl bearing at least one hydroxyl substituent; —$(CH_2)R^a$, wherein $R^a$ is $C_5$ to $C_{10}$ cycloalkyl; aryl; benzyl; —$CH_2CH_2OR^1$, —$CH(CH_2OR^1)_2$, —$C(CH_2OR^1)_3$, or $CH_2CH_2N(R^1)_2$; or when R is —$CH_2CH_2N(R^1)_2$, each $R^1$ can be taken together to form a heterocyclic ring;

$R^1$ is H, $C_1$ to $C_{10}$ alkyl, —COR, or —$CO_2R$;

X is halogen, CN, OH, SH, =$CHR^1$;

A is $C_1$ to $C_{10}$ alkyl bearing at least one hydroxyl substituent; and

L is $C_1$-$C_6$ alkylene wherein optionally at least one $CH_2$ unit can be replaced with O or S with the proviso that the compound:

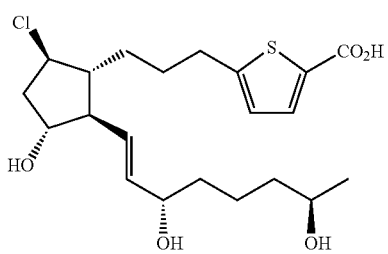

is not included.

In some embodiments of the invention, X is halogen. In certain embodiments, X is Cl.

In some embodiments of the invention, L is $C_1$-$C_6$ alkylene. In certain embodiments, L is $C_3$ alkylene.

In some embodiments of the invention, A is $C_4$-$C_6$ alkyl. In certain embodiments, A is $C_5$ alkyl.

In some embodiments of the invention, A bears one hydroxyl substituent. In some embodiments, A bears multiple hydroxyl substituent. As used herein, the term "multiple" means "more than one".

In some embodiments of the invention, R is H or $C_1$-$C_{10}$ alkyl. In certain embodiments, R is H. In some embodiments, R is $C_1$-$C_{10}$ alkyl bearing multiple hydroxyl substituents. In these embodiments of the invention, R bears substituents having multiple hydroxyl groups, such as, for example, glycerol, sorbitol, mannitol, erythritol, xylitol, and the like.

In some embodiments of the invention, $R^1$ is H or $C_1$ to $C_{10}$ alkyl. In certain embodiments, $R^1$ is H.

In some embodiments, the $R^1$ on the oxygen on the cyclopentyl ring, the $R^1$ on the oxygen at the allylic position on the bottom ring, and the $R^1$ that in some embodiments can form part of R can be, independently, H, $C_1$ to $C_{10}$ alkyl, —COR, or —$CO_2R$.

In some embodiments wherein R is —$CH_2CH_2N(R^1)_2$, each $R^1$ can be taken together to form a heterocyclic ring. In some embodiments, each $R^1$ (taken together with the nitrogen atom to which each $R^1$ is attached) forms a morpholino moiety.

Exemplary compounds of the invention include, but are not limited to, compounds having any one of the following structures:

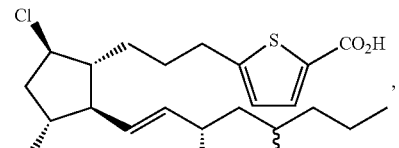

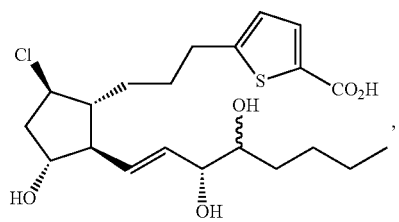

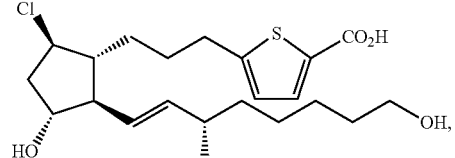

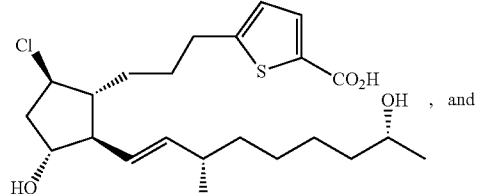

, and

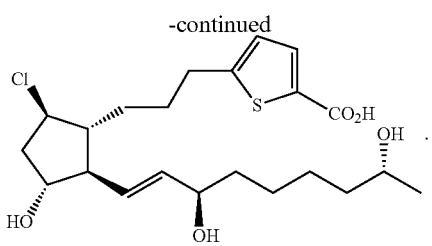

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release.

Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the invention compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the invention compound or compounds is preferably in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate.

A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001 to 5 |
| preservative | 0 to 0.10 |
| vehicle | 0 to 40 |
| tonicity adjustor | 1 to 10 |
| buffer | 0.01 to 10 |
| pH adjustor | q.s. pH 4.5 to 7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

For the treatment of glaucoma, combination treatment with the following classes of drugs are contemplated:

β-Blockers (or β-adrenergic antagonists) including carteolol, levobunolol, metiparanolol, timolol hemihydrate, timolol maleate, β1-selective antagonists such as betaxolol, and the like, or pharmaceutically acceptable salts or prodrugs thereof;

Adrenergic Agonists including
  non-selective adrenergic agonists such as epinephrine borate, epinephrine hydrochloride, and dipivefrin, and the like, or pharmaceutically acceptable salts or prodrugs thereof; and
  $\alpha_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including
  direct acting cholinergic agonists such as carbachol, pilocarpine hydrochloride, pilocarbine nitrate, pilocarpine, and the like, or pharmaceutically acceptable salts or prodrugs thereof;
  chlolinesterase inhibitors such as demecarium, echothiophate, physostigmine, and the like, or pharmaceutically acceptable salts or prodrugs thereof;

Glutamate Antagonists and other neuroprotective agents such as $Ca^{2+}$ channel blockers such as memantine, amantadine, rimantadine, nitroglycerin, dextrophan, dextromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;

Prostamides such as bimatoprost or prodrugs thereof; and

Prostaglandins including travoprost, UFO-21, chlorprostenol, fluprostenol, 13,14-dihydro-chloprostenol, isopropyl unoprostone, latanoprost and the like.

Cannabinoids including CB1 agonists such as WIN-55212-2 and CP-55940 and the like, or pharmaceutically acceptable salts or prodrugs thereof.

For treatment of diseases affecting the eye including glaucoma, these compounds can be administered topically, periocularly, intraocularly, or by any other effective means known in the art.

The compounds of the invention can be prepared in a variety of ways well known to those skilled in the art. Schemes 1 to 5 set forth below outline exemplary synthetic routes to certain exemplary compounds of the invention.

SCHEME 1

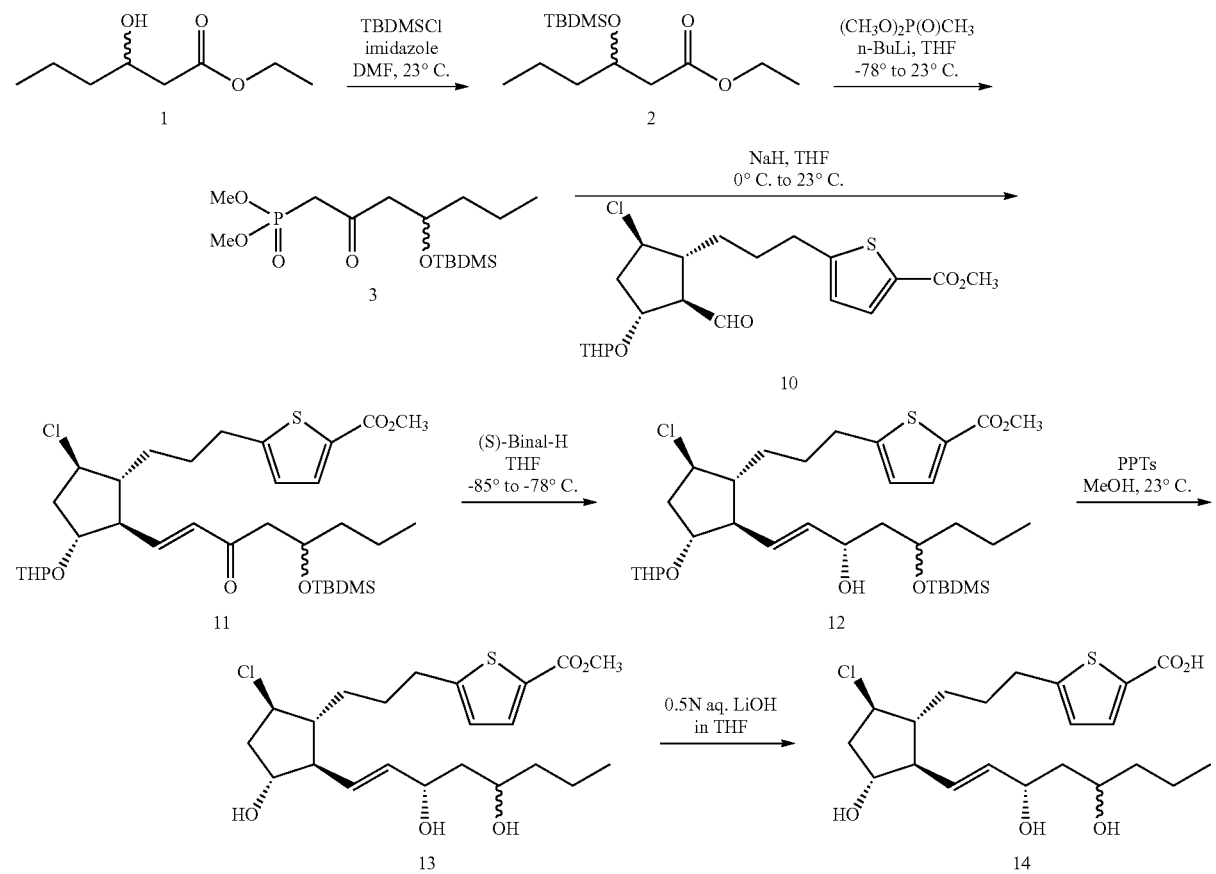

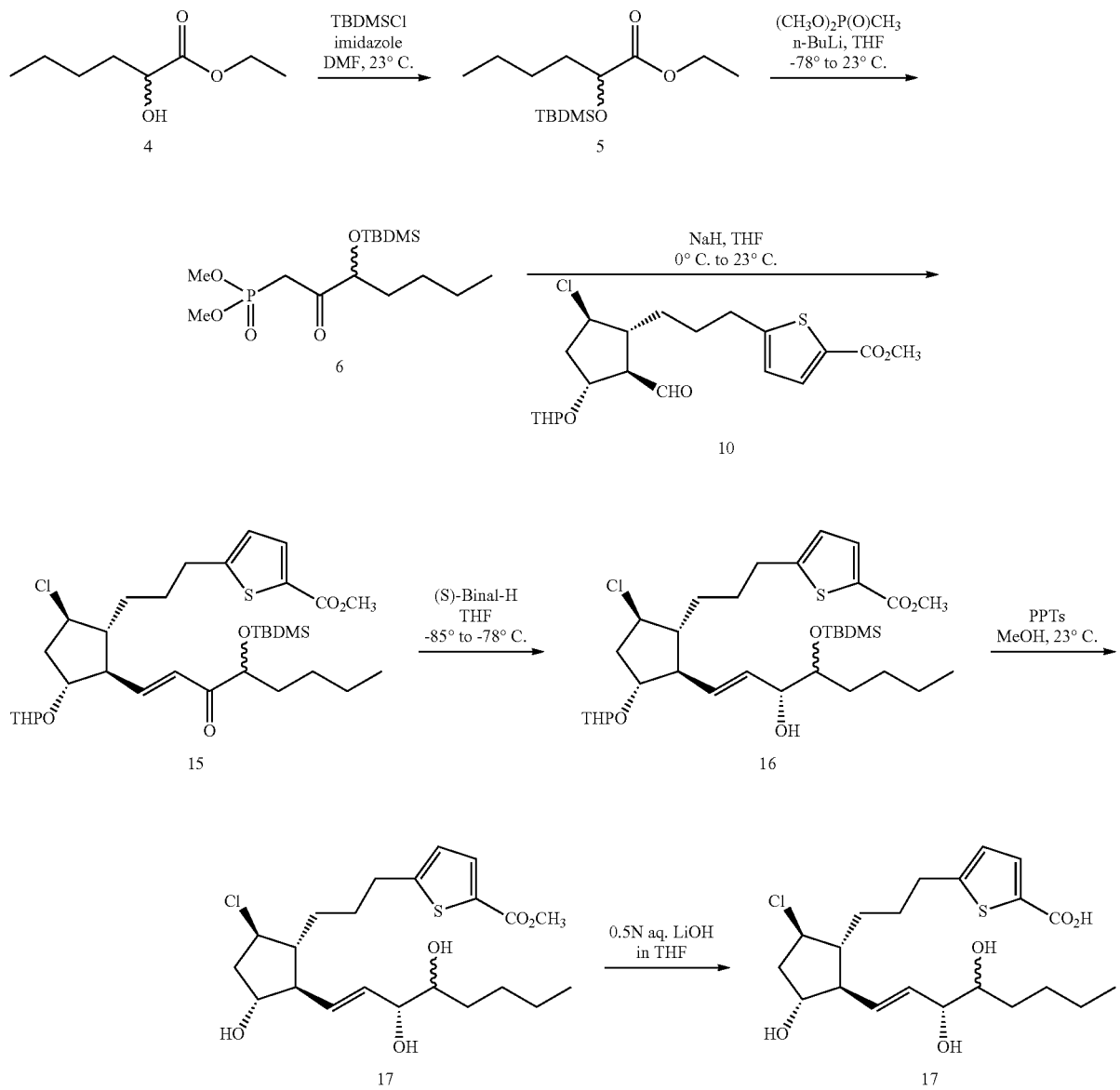
SCHEME 2
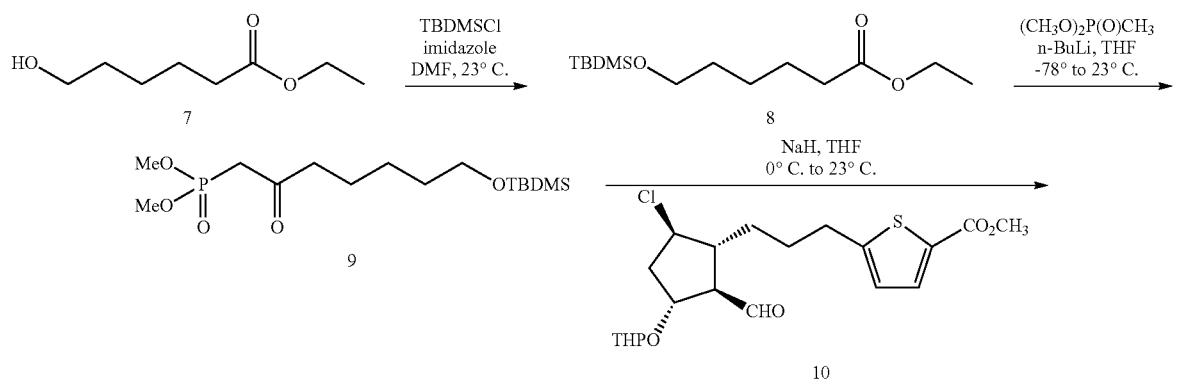
SCHEME 3

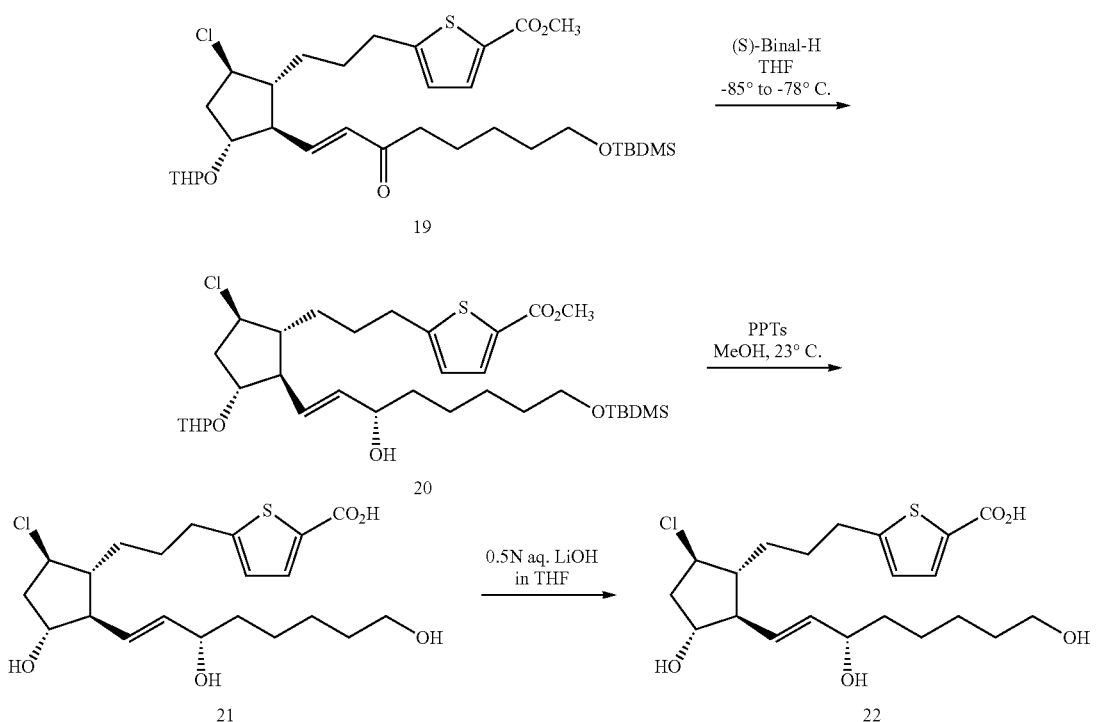
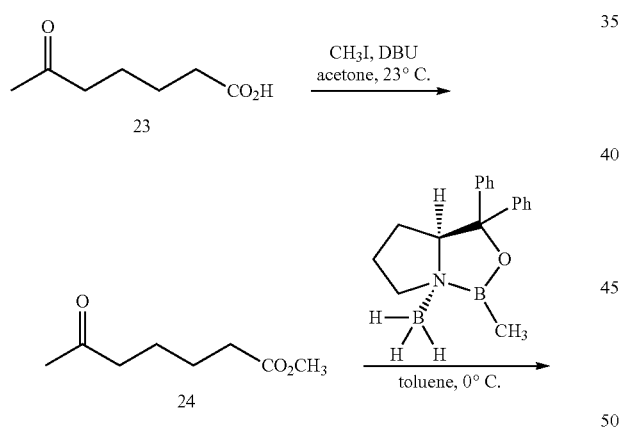
SCHEME 4
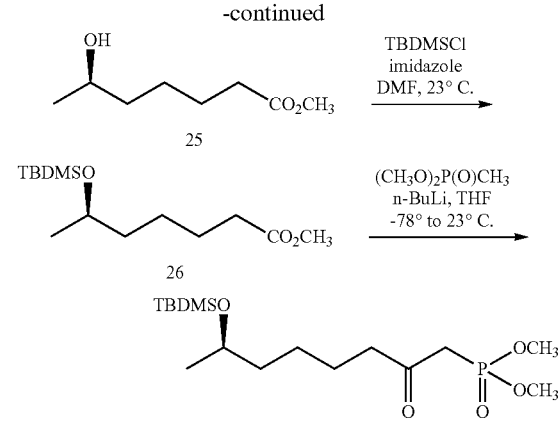
SCHEME 5
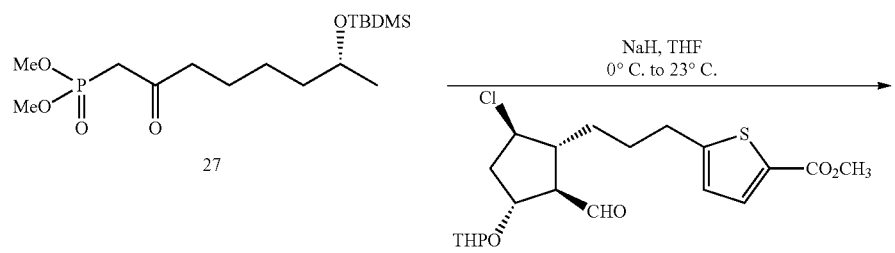

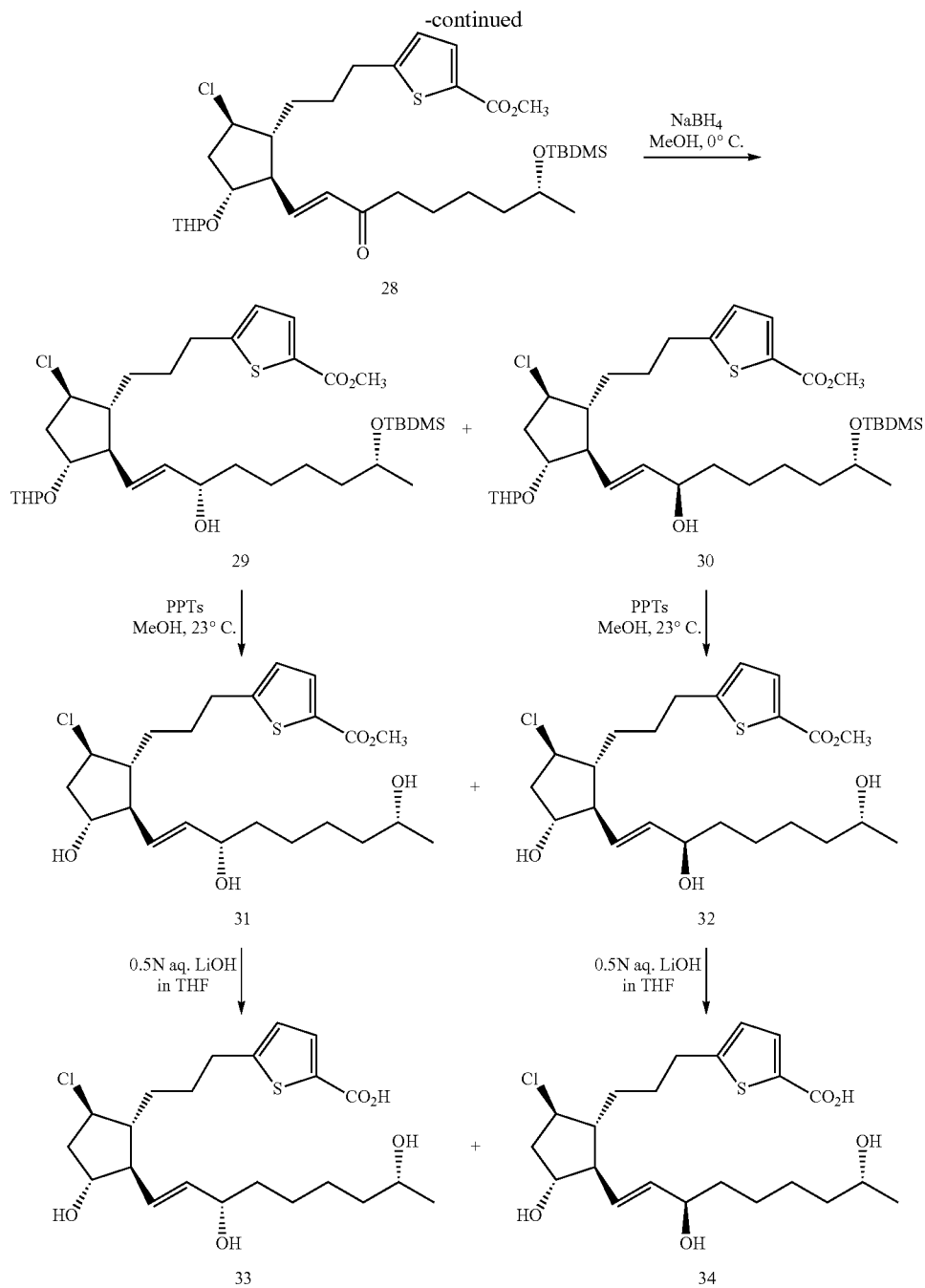

Those skilled in the art will appreciate that many additional compounds that fall under the scope of the invention can be prepared by performing various common chemical reactions. Details of certain specific chemical transformations are provided in the examples.

Those skilled in the art will be able to routinely modify and/or adapt the preceding schemes to synthesize any compounds described herein.

The present invention is not to be limited in scope by the exemplified embodiments which are intended as illustrations of single aspects of the invention only. Indeed, various modifications of the invention in addition to those described herein will become apparent to those skilled in the art from the foregoing description.

EXAMPLES

The following examples are intended only to illustrate the invention and should in no way be construed as limiting the invention.

SYNTHETIC PROCEDURES

Ethyl 3-((tert-butyldimethylsilyl)oxy)hexanoate (2)

A solution of ethyl 3-hydroxyhexanoate 1 (2.0 g, 12.5 mmol), imidazole (1.09 g, 18.7 mmol), and tert-butyldimethylsilyl chloride (2.26 g, 15.0 mmol) in DMF (25 mL) was stirred at 23° C. After 16 h the reaction was diluted with $Et_2O$ and then washed with 1N HCl, saturated aqueous $NaHCO_3$ and brine. The organic portion was dried (MgSO$_4$), filtered and concentrated in vacuo. The residue was purified by flash column chromatography (silica gel, 100% hex followed by 19:1 hex/EtOAc) afforded 2.8 g (82%) of silyl ether 2 (see Scheme 1).

Dimethyl(4-((tert-butyldimethylsilyl)oxy)-2-oxoheptyl)phosphonate (3)

n-Butyllithium (6.8 mL of a 1.6M solution in THF, 10.94 mmol) was added to a solution of dimethyl methylphosphonate (1.2 mL, 10.94 mmol) in THF (22 mL) at −78° C. After 0.5 h a solution of the ester 2 (2.0 g, 7.29 mmol) in THF (4 mL) was added. The reaction solution was allowed to warm to room temperature overnight on its own accord. After 16 h the reaction was quenched with saturated aqueous ammonium chloride and extracted with EtOAc. The organic portion was washed with brine, dried (MgSO$_4$), filtered and concentrated in vacuo. The residue was purified by flash column chromatography (silica gel, 2:1 hex/EtOAc followed by 1:1 hex/EtOAc) afforded 0.93 g (36%) of phosphonate 3 (see Scheme 1).

Methyl 5-(3-((1R,2R,3R,5R)-2-((E)-5-((tert-butyldimethylsilyl)oxy)-3-oxooct-1-en-1-yl)-5-chloro-3-((tetrahydro-2H-pyran-2-yl)oxy)cyclopentyl)propyl)thiophene-2-carboxylate (11)

To a suspension of 105 mg of sodium hydride (60% oil dispersion, 2.62 mmol) in THF (8 mL) at 0° C. was added a solution of phosphonate 3 (925 mg, 2.62 mmol) in THF (4 mL). The mixture was stirred at 0° C. for 30 min before a solution of aldehyde 10 (987 mg, 2.38 mmol; see U.S. Pat. No. 7,429,669 and U.S. Pat. No. 8,158,676, the contents of each of which is incorporated by reference) in THF (4 mL) was added dropwise. The reaction was allowed to warm to room temperature, stirred an additional 3 h and was then quenched with saturated aqueous ammonium chloride. The reaction was extracted with EtOAc and the organic portion was washed with brine, dried (MgSO$_4$), filtered and then concentrated in vacuo. The residue was purified by flash column chromatography (silica gel, 4:1 hex/EtOAc) afforded 1.52 g (100%) of enone 11 (see Scheme 1).

Methyl 5-(3-((1R,2R,3R,5R)-2-((3S,E)-5-((tert-butyldimethylsilyl)loxy)-3-hydroxyoct-1-en-1-yl)-5-chloro-3-((tetrahydro-2H-pyran-2-yl)oxy)cyclopentyl)-propyl)thiophene-2-carboxylate (12)

A freshly prepared solution of absolute ethanol (7.1 mL of a 1.0 M solution in THF, 7.1 mmol) was added dropwise at 23° C. to lithium aluminum hydride (7.1 mL of a 1.0 M solution in THF, 7.1 mmol) in a 200 mL oven dried flask. After 15 min a solution of (S)-(−)-1,1'-binaphthol (2.08 g, 7.26 mmol) in THF (10 mL) was added dropwise. The resultant milky, white solution was cooled to −85° C. and a solution of the enone 11 (1.52 g, 2.38 mmol) in THF (8 mL) was added over a period of 5 min. The reaction solution was stirred for 1 h, warmed to −78° C. and then stirred for an additional 3 h. The reaction was then quenched by careful addition of 3.0 mL of MeOH and then allowed to warm to room temperature. The resultant solution was diluted with EtOAc and washed with saturated aqueous sodium bicarbonate followed by brine. The organic portion was dried (MgSO$_4$), filtered and concentrated in vacuo. The residue was purified by flash column chromatography (silica gel, 4:1 hex/EtOAc) afforded 1.32 g (87%) of alcohol 12 (see Scheme 1).

Methyl 5-(3-((1R,2R,3R,5R)-5-chloro-2-((3S,E)-3,5-dihydroxyoct-1-en-1-yl)-3-hydroxycyclopentyl)propyl)thiophene-2-carboxylate (13)

A solution of THP-ether 12 (100 mg, 0.156 mmol) and pyridinium p-toluenesulfonate (39.2 mg, 0.156 mmol) in MeOH (3.0 mL) was stirred at 23° C. for 48 h. The solvent was removed in vacuo. The residue was diluted with EtOAc and washed with 1N HCl, saturated aqueous sodium bicarbonate and brine. The organic portion was dried (MgSO$_4$), filtered and concentrated in vacuo. The residue was purified by flash column chromatography (silica gel, 100% EtOAc followed by 19:1 EtOAc/MeOH) afforded 53 mg (76%) of triol 13 (see Scheme 1).

5-(3-((1R,2R,3R,5R)-5-chloro-2-((3S,E)-3,5-dihydroxyoct-1-en-1-yl)-3-hydroxycyclopentyl)propyl)thiophene-2-carboxylic acid (14)

Lithium hydroxide (0.32 mL of a 0.5N solution in H$_2$O, 0.16 mmol) was added to a solution of the ester 13 (36 mg, 0.081 mmol) in THF (0.64 mL) at 23° C. After stirring for 24 h the reaction mixture was acidified with 1N HCl and extracted with EtOAc. The organic portion was washed with brine (2×), dried (Na$_2$SO$_4$), filtered and concentrated in vacuo to provide 27.6 mg (79%) of the free acid 14 (see Scheme 1).

Ethyl 2-((tert-butyldimethylsilyl)oxy)hexanoate (5)

Ethyl 2-((tert-butyldimethylsilyl)oxy)hexanoate 5 (2.54 g) was prepared in 74% yield using ethyl 2-hydroxyhexanoate 4 according to the procedures described for compound 2 in above (See Schemes 1 and 2).

Dimethyl(3-((tert-butyldimethylsilyl)oxy)-2-oxoheptyl)phosphonate (6)

Dimethyl (3-((tert-butyldimethylsilyl)oxy)-2-oxoheptyl) phosphonate 6 (1.56 g) was prepared in 61% yield using compound 5 according to the procedures described for compound 3 (see Schemes 1 and 2).

Methyl 5-(3-((1R,2R,3R,5R)-2-((E)-4-((tert-butyldimethylsilyl)oxy)-3-oxooct-1-en-1-yl)-5-chloro-3-((tetrahydro-2H-pyran-2-yl)oxy)cyclopentyl)propyl)thiophene-2-carboxylate (15)

Compound 15 (1.32 g) was prepared in 86% yield by employing dimethyl (3-((tert-butyldimethylsilyl)oxy)-2-oxoheptyl)phosphonate 6 and aldehyde 10 according to the procedures described for compound 11 (see Schemes 1 and 2).

Methyl 5-(3-((1R,2R,3R,5R)-2-((3R,E)-4-((tert-butyldimethylsily)loxy)-3-hydroxyoct-1-en-1-yl)-5-chloro-3-((tetrahydro-2H-pyran-2-yl)oxy)cyclopentyl)-propyl)thiophene-2-carboxylate (16)

Compound 16 (1.13 g) was prepared in 85% yield using compound 15 according to the procedures described for compound 12 (see Schemes 1 and 2).

Methyl 5-(3-((1R,2R,3R,5R)-5-chloro-2-((3R,E)-3,4-dihydroxyoct-1-en-1-yl)-3-hydroxycyclopentyl)propyl)thiophene-2-carboxylate (17)

Compound 17 (66.6 mg) was prepared in 96% yield using compound 16 according to the procedures described for compound 13 (see Schemes 1 and 2).

5-(3-((1R,2R,3R,5R)-5-chloro-2-((3R,E)-3,4-dihydroxyoct-1-en-1-yl)-3-hydroxycyclopentyl)propyl)thiophene-2-carboxylic acid (18)

Compound 18 (60.9 mg) was prepared in 95% yield using compound 17 according to the procedures described for compound 14 (see Schemes 1 and 2).

Ethyl 6-((tert-butyldimethylsilyl)oxy)hexanoate (8)

Ethyl 6-((tert-butyldimethylsilyl)oxy)hexanoate 8 (3.08 g) was prepared in 90% yield using ethyl 6-hydroxyhexanoate 7 according to the procedures described for compound 2 in above (see Schemes 1-3).

Dimethyl(7-((tert-butyldimethylsilyl)oxy)-2-oxoheptyl)phosphonate (9)

Dimethyl(3-((tert-butyldimethylsilyl)oxy)-2-oxoheptyl)phosphonate 9 (1.55 g) was prepared in 60% yield using compound 8 according to the procedures described for compound 3 (see Schemes 1-3).

Methyl 5-(3-((1R,2R,3R,5R)-2-((E)-8-(tert-butyldimethylsilyl)oxy)-3-oxooct-1-en-1-yl)-5-chloro-3-((tetrahydro-2H-pyran-2-yl)oxy)cyclopentyl)propyl)thiophene-2-carboxylate (19)

Compound 19 (1.14 g) was prepared in 69% yield by employing dimethyl (7-((tert-butyldimethylsilyl)oxy)-2-oxoheptyl)phosphonate 9 and aldehyde 10 according to the procedures described for compound 11 (see Schemes 1-3).

Methyl 5-(3-((1R,2R,3R,5R)-2-((S,E)-8-((tert-butyldimethylsily)loxy)-3-hydroxyoct-1-en-1-yl)-5-chloro-3-((tetrahydro-2H-pyran-2-yl)oxy)cyclopentyl)-propyl)thiophene-2-carboxylate (20)

Compound 20 (1.10 g) was prepared in 96% yield using compound 19 according to the procedures described for compound 12 (see Schemes 1-3).

Methyl 5-(3-((1R,2R,3R,5R)-5-chloro-2-((S,E)-3,8-dihydroxyoct-1-en-1-yl)-3-hydroxycyclopentyl)propyl)thiophene-2-carboxylate (21)

Compound 21 (65.9 mg) was prepared in 95% yield using compound 20 according to the procedures described for compound 13 (see Schemes 1-3).

5-(3-((1R,2R,3R,5R)-5-chloro-2-((S,E)-3,8-dihydroxyoct-1-en-1-yl)-3-hydroxycyclopentyl)propyl)thiophene-2-carboxylic acid (22)

Compound 22 (31.8 mg) was prepared in 82% yield using compound 21 according to the procedures described for compound 14 (see Schemes 1-3).

Methyl 6-oxoheptanoate (24)

1,8-Diazabicyclo[5.4.0]undec-7-ene (3.4 mL, 22.86 mmol) was added to a solution of 6-oxoheptanoic acid 23 (1.1 g, 7.63 mmol) in acetone (15 mL) at 23° C. After stirring for 15 min iodomethane (2.4 mL, 38.3 mmol) was added. The reaction was stirred for 1 h and then the solvent was removed in vacuo. The residue was purified by flash column chromatography (silica gel, 7:3 hex/EtOAc) to provide 1.18 g (95%) of the methyl ester 24 (see scheme 4).

(R)-methyl 6-hydroxyheptanoate (25)

(S)-methyloxazaborolidine (8.77 g, 31.63 mmol) dissolved in 30 mL of toluene. The solution was cooled to 0° C. and the borane tetrahydrofuran complex (31.6 mL of 1.0M solution in THF, 31.6 mmol) was added. After 30 min the ketone 24 (5.0 g, 31.63 mmol) was added. The reaction solution was stirred for 4 h and was then quenched by slow addition of saturated aqueous ammonium chloride. The resultant mixture was extracted with EtOAc (2×). The combined organic portions were washed with brine, dried (MgSO$_4$), filtered and concentrated in vacuo. Flash column chromatography (silica gel, 3:1 hex/EtOAc) afforded 2.58 g (51%) of the alcohol 25 (see scheme 4).

(R)-Methyl 6-((tert-butyldimethylsilyl)oxy)heptanoate (26)

A solution of alcohol 25 (2.53 g, 15.89 mmol), imidazole (1.9 g, 27.9 mmol), and tert-butyldimethylsilyl chloride (2.4 g, 15.89 mmol) in DMF (32 mL) was stirred at 23° C. After 16 h the reaction was diluted with Et$_2$O and then washed with 1N HCl, saturated aqueous NaHCO$_3$ and brine. The organic portion was dried (MgSO$_4$), filtered and concentrated in vacuo. The residue was purified by flash column chromatography (silica gel, 9:1 hex/EtOAc) afforded 3.11 g (71%) of silyl ether 26 (see scheme 4).

(R)-Dimethyl(7-((tert-butyldimethylsilyl)oxy)-2-oxooctyl)phosphonate (27)

n-Butyllithium (14.2 mL of a 1.6M solution in THF, 22.68 mmol) was added to a solution of dimethyl methylphosphonate (2.5 mL, 22.68 mmol) in THF (18 mL) at −78° C. After 0.5 h a solution of the ester 26 (3.11 g, 11.34 mmol) in THF (5 mL) was added. The reaction solution was allowed to warm to room temperature overnight on its own accord. After 16 h the reaction was quenched with saturated aqueous ammonium chloride and extracted with EtOAc. The organic portion was washed with brine, dried (MgSO$_4$), filtered and concentrated in vacuo. The residue was purified by flash column chromatography (silica gel, 2:3 hex/EtOAc) afforded 3.75 g (90%) of phosphonate 27 (see scheme 4).

Methyl 5-(3-((1R,2R,3R,5R)-2-((R,E)-8-((tert-butyldimethylsilyl)oxy)-3-oxonon-1-en-1-yl)-5-chloro-3-((tetrahydro-2H-pyran-2-yl)oxy)cyclopentyl)propyl)thiophene-2-carboxylate (28)

To a suspension of 60 mg of sodium hydride (60% oil dispersion, 2.62 mmol) in THF (8 mL) at 0° C. was added a solution of phosphonate 27 (960 mg, 2.62 mmol) in THF (4 mL). The mixture was stirred at 0° C. for 30 min before a solution of aldehyde 10 (990 mg, 2.38 mmol) in THF (4 mL) was added dropwise. The reaction was allowed to warm to room temperature, stirred an additional 3 h and was then quenched with saturated aqueous ammonium chloride. The reaction was extracted with EtOAc and the organic portion was washed with brine, dried (MgSO$_4$) and then concentrated in vacuo. The residue was purified by flash column chromatography (silica gel, 4:1 hex/EtOAc) afforded 1.64 g (95%) of enone 28 (see Scheme 5).

Methyl 5-(3-((1R,2R,3R,5R)-2-((3S,8R,E)-8-((tert-butyldimethylsilyl)oxy)-3-hydroxynon-1-en-1-yl)-5-chloro-3-((tetrahydro-2H-pyran-2-yl)oxy)cyclopentyl)propyl)thiophene-2-carboxylate (29) and methyl 5-(3-((1R,2R,3R,5R)-2-((3R,8R,E)-8-((tert-butyldimethylsilyl)oxy)-3-hydroxynon-1-en-1-yl)-5-chloro-3-((tetrahydro-2H-pyran-2-yl)oxy)cyclopentyl)propyl)thiophene-2-carboxylate (30)

Sodium tetrahydridoborate (95 mg, 2.51 mmol) was added to a solution of the enone 28 (1.64 mg, 2.51 mmol) in MeOH (5 mL) at 0° C. After 4 h the reaction was quenched with saturated aqueous ammonium chloride. The resultant mixture was extracted with EtOAc (2x). The combined organics were washed with brine, dried (MgSO$_4$), filtered and concentrated in vacuo. The residue was purified by flash column chromatography (silica gel, 4:1 hex/EtOAc) afforded 235 mg (14%) of both pure S-alcohol 29 and 193 mg (12%) of (R)-alcohol 30 (see Scheme 5).

Methyl 5-(3-((1R,2R,3R,5R)-5-chloro-2-((3S,8R,E)-3,8-dihydroxynon-1-en-1-yl)-3-hydroxycyclopentyl)propyl)thiophene-2-carboxylate (31)

A solution of THP-ether 29 (193 mg, 0.30 mmol) and pyridinium p-toluenesulfonate (15 mg, 0.060 mmol) in MeOH (2.0 mL) was stirred at 23° C. for 48 h. The solvent was removed in vacuo. The residue was diluted with EtOAc and washed with 1N HCl, saturated aqueous sodium bicarbonate and brine. The organic portion was dried (MgSO$_4$), filtered and concentrated in vacuo. The residue was purified by flash column chromatography (silica gel, 3:1 EtOAc/hex) afforded 111 mg (81%) of triol 31 (see Scheme 5).

Methyl 5-(3-((1R,2R,3R,5R)-5-chloro-2-((3R,8R,E)-3,8-dihydroxynon-1-en-1-yl)-3-hydroxycyclopentyl)propyl)thiophene-2-carboxylate (32)

In accordance with the procedures described above for preparation of triol 31 the THP-ether 30 (235 mg) was converted in 75% yield to triol 32 (see Scheme 5).

5-(3-((1R,2R,3R,5R)-5-Chloro-2-((3S 8R,E)-3,8-dihydroxynon-1-en-1-yl)-3-hydroxycyclopentyl)propyl)thiophene-2-carboxylic acid (33)

Lithium hydroxide (1.2 mL of a 0.5N solution in H$_2$O, 0.605 mmol) was added to a solution of the ester 31 (111 mg, 0.242 mmol) in THF (0.5 mL) at 23° C. After stirring for 24 h the reaction mixture was acidified with 1N HCl and extracted with EtOAc. The organic portion was washed with brine (2x), dried (Na$_2$SO$_4$), filtered and concentrated in vacuo. Purification of the residue by flash column chromatography (silica gel, 4:1 CH$_2$Cl$_2$/MeOH) provided 90 mg (84%) of the free acid 33 (see Scheme 5).

5-(3-((1R,2R,3R,5R)-5-chloro-2-((3R,8R,E)-3,8-dihydroxynon-1-en-1-yl)-3-hydroxycyclopentyl)propyl)thiophene-2-carboxylic acid (34)

In accordance with the procedures described above for preparation of free acid 33 the ester 32 (123 mg) was converted in 82% yield to free acid 34 (see Scheme 5).

BIOLOGICAL DATA

Data from running binding and activity studies on the compounds of the invention were carried out as described in U.S. Pat. No. 7,427,685, the contents of which are incorporated herein by reference. The results set forth below in Tables 1 and 2 demonstrate that the compounds disclosed herein are selective prostaglandin EP$_2$ agonists, and are thus useful for the treatment of glaucoma, ocular hypertension, inflammatory bowel disease, and the other diseases or conditions disclosed herein.

TABLE 1

| Entry | Compound | EP$_2$ cAMP EC$_{50}$ (nM) | EP$_2$ Ca$^{2+}$ signal EC$_{50}$ (nM) | EP$_2$ Binding EC$_{50}$ (nM) | EP4 Ca$^{2+}$ signal EC$_{50}$ (nM) | EP4 Binding EC$_{50}$ (nM) | EP$_1$ EC$_{50}$ (nM) | EP$_3$ EC$_{50}$ (nM) | DP EC$_{50}$ (nM) | TP EC$_{50}$ (nM) |
|---|---|---|---|---|---|---|---|---|---|---|
| 1 | 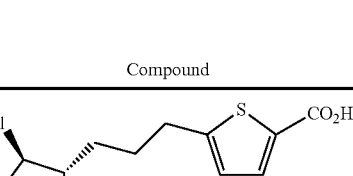 | 0.06 | 7.4 | 66 | 145 | 2347 | 724 | 499 | 6792 | NA |
| 2 | 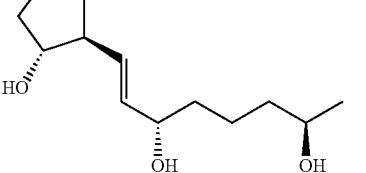 | 3 | 27 | 716 | 23 | 434 | 1243 | 690 | 2255 | 4796 |

TABLE 1-continued

| Entry | Compound | EP2 cAMP EC50 (nM) | EP2 Ca2+ signal EC50 (nM) | EP2 Binding EC50 (nM) | EP4 Ca2+ signal EC50 (nM) | EP4 Binding EC50 (nM) | EP1 EC50 (nM) | EP3 EC50 (nM) | DP EC50 (nM) | TP EC50 (nM) |
|---|---|---|---|---|---|---|---|---|---|---|
| 3 | (structure) | 2.3 | 9 | 148 | 45 | 490 | NA | NA | 886 | NA |
| 4 | (structure) | 0.4 | 4 | 147 | 68 | 1127 | 101 | 129 | 3350 | 7567 |

TABLE 2

| Entry | Compound | EP2 cAMP EC50 (nM) | EP2 Ca2+ signal EC50 (nM) | EP2 Binding EC50 (nM) | EP4 Ca2+ signal EC50 (nM) | EP4 Binding EC50 (nM) | EP1 EC50 (nM) | EP3 EC50 (nM) | DP EC50 (nM) | TP EC50 (nM) |
|---|---|---|---|---|---|---|---|---|---|---|
| 1 | (structure) | 1.4 | 29 | 363 | 455 | >$10^4$ | 207 | 222 | 4523 | NA |
| 2 | (structure) | 14 | 328 | 365 | >$10^4$ | 3412 | 4218 | 7135 | NA | NA |

As will be evident to those skilled in the art, individual isomeric forms can be obtained by separation of mixtures thereof in conventional manner. For example, in the case of diasteroisomeric isomers, chromatographic separation can be employed.

Compound names were generated with ACDLabs version 12.5. Some of the intermediate and reagent names used in the examples were generated with software such as Chem Bio Draw Ultra version 12.0 or Auto Nom 2000 from MDL ISIS Draw 2.5 SP1.

The invention claimed is:
1. A compound having the structure:

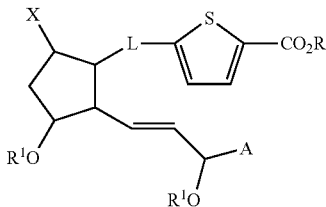

or a pharmaceutically acceptable salt, enantiomer, or diastereomer thereof, wherein:
R is H; $C_1$ to $C_{10}$ alkyl; $C_1$ to $C_{10}$ alkyl bearing at least one hydroxyl substituent; —$(CH_2)R^a$, wherein $R^a$ is $C_5$ to $C_{10}$ cycloalkyl; aryl; benzyl; —$CH_2CH_2OR^1$, —$CH(CH_2OR^1)_2$, —$C(CH_2OR^1)_3$, or $CH_2CH_2N(R^1)_2$;
$R^1$ is H, $C_1$ to $C_{10}$ alkyl, —COR, or —$CO_2R$; or, when R is —$CH_2CH_2N(R^1)_2$, each $R^1$ can be taken together to form a morpholine ring;
X is halogen, CN, OH, SH, =$CHR^1$;
A is selected from the group consisting of:

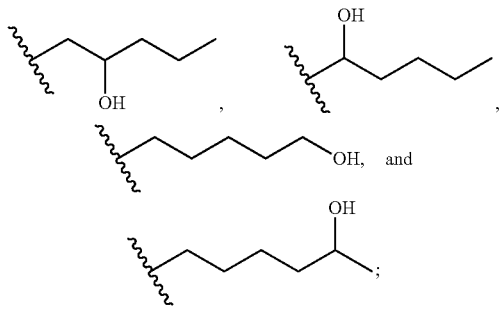

and
L is $C_1$-$C_6$ alkylene wherein optionally at least one $CH_2$ unit can be replaced with O or S.
2. The compound of claim 1 wherein X is halogen.
3. The compound of claim 2 wherein X is Cl.
4. The compound of claim 1 wherein L is $C_1$-$C_6$ alkylene.
5. The compound of claim 4 wherein L is $C_3$ alkylene.
6. The compound of claim 1 wherein R is $C_1$ to $C_{10}$ alkyl bearing at least one hydroxyl substituent.
7. The compound of claim 1 wherein R is $C_1$ to $C_{10}$ alkyl bearing multiple hydroxyl substituents.
8. The compound of claim 1 wherein R is H or $C_1$ to $C_{10}$ alkyl.
9. The compound of claim 1 wherein R is H.
10. The compound of claim 1 wherein $R^1$ is H or $C_1$ to $C_{10}$ alkyl.
11. The compound of claim 1 wherein $R^1$ is H.
12. The compound of claim 1 wherein R is —$CH_2CH_2N(R^1)_2$.
13. The compound of claim 12 wherein R is ethlymorpholino.
14. The compound of claim 1 having any one of the following structures:

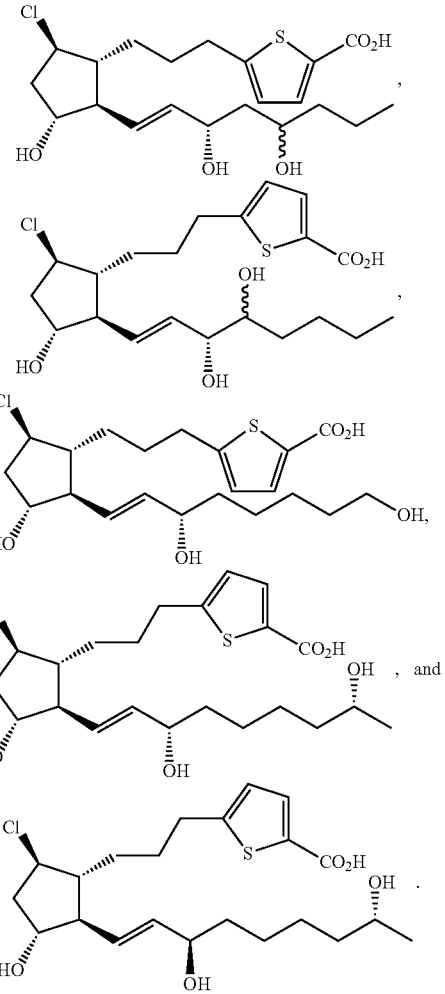

or a pharmaceutically acceptable salt thereof.
15. A pharmaceutical composition comprising at least one compound according to claim 1 and a pharmaceutically acceptable carrier, wherein the composition is a liquid which is ophthalmically acceptable.
16. A method of treating glaucoma or ocular hypertension comprising administering to a subject in need thereof a therapeutically effective amount of a compound according to claim 1.
17. The method of claim 16 wherein the subject is human.
18. A kit comprising the composition of claim 15, a container, and instructions for administration of the composition to a subject in need thereof for the treatment of glaucoma or ocular hypertension.

* * * * *